US011717352B2

(12) United States Patent
Hareland

(10) Patent No.: US 11,717,352 B2
(45) Date of Patent: Aug. 8, 2023

(54) NAVIGATION GUIDANCE METHOD FOR COMPLEX CATHETERS

(71) Applicant: Medtronic, Inc., Minneapolis, MN (US)

(72) Inventor: Scott A. Hareland, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 541 days.

(21) Appl. No.: 16/890,414

(22) Filed: Jun. 2, 2020

(65) Prior Publication Data

US 2020/0289209 A1    Sep. 17, 2020

Related U.S. Application Data

(62) Division of application No. 15/259,683, filed on Sep. 8, 2016, now Pat. No. 10,702,342.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/066* (2013.01); *A61B 5/068* (2013.01); *A61B 5/6852* (2013.01);
(Continued)

(58) Field of Classification Search
CPC ... A61B 34/20; A61B 5/6852; A61B 18/1492; A61B 5/068; A61B 5/066; A61B 90/37;
(Continued)

(56) References Cited

U.S. PATENT DOCUMENTS 6,129,669 A    10/2000 Panescu et al.
6,873,718 B2    3/2005 O'Donnell et al.
(Continued)

OTHER PUBLICATIONS

Park et al., Intra-Procedural Imaging of Left Atrium and Pulmonary Veins With Rotational Angiography: A Comparison of Anatomy Obtained by Pre-Procedural Cardiac Computed Tomography and Trans-Thoracic Echocardiography, , Int J Cardiovasc Imaging (Year: 2013).*

(Continued)

*Primary Examiner* — Joseph M Santos Rodriguez
*Assistant Examiner* — Amy Shafqat
(74) *Attorney, Agent, or Firm* — Michael Best & Friedrich LLP

(57) ABSTRACT

A method and system for determining a target location for a medical device having complex geometry relative to an anatomical feature, and for navigating and positioning the medical device at the target location. The system may include a medical device including a treatment element having a centroid, one or more navigation electrodes, and a longitudinal axis and a navigation system in communication with the one or more navigation electrodes, the navigation system including a processing unit. The processing unit may be programmed to define a plane that approximates a surface of the anatomical feature, define a centroid of the anatomical feature, define a vector that is normal to the plane and extends away from the centroid of the anatomical feature, and determine a target location for the treatment element of the medical device based on the vector to assist the user in placing the device for treatment.

19 Claims, 5 Drawing Sheets

(51) Int. Cl.
  *A61B 90/00* (2016.01)
  *A61B 18/14* (2006.01)
  *A61B 5/00* (2006.01)
  *A61M 25/01* (2006.01)
  *A61B 18/00* (2006.01)

(52) U.S. Cl.
  CPC .......... *A61B 18/1492* (2013.01); *A61B 90/37* (2016.02); *A61B 2018/0022* (2013.01); *A61B 2018/00214* (2013.01); *A61B 2018/00345* (2013.01); *A61B 2034/2053* (2016.02); *A61B 2034/2065* (2016.02); *A61B 2090/365* (2016.02); *A61M 2025/0166* (2013.01)

(58) Field of Classification Search
  CPC .... A61B 2018/0022; A61B 2034/2053; A61B 2090/365; A61B 2034/2065; A61B 2018/00214; A61B 2018/00345; A61M 2025/0166
  See application file for complete search history.

(56) References Cited

U.S. PATENT DOCUMENTS

| | | | |
|---|---|---|---|
| 6,926,714 B1 | 8/2005 | Sra | |
| 6,947,785 B1 | 9/2005 | Beatty et al. | |
| 7,565,190 B2 | 7/2009 | Okerlund et al. | |
| 7,681,579 B2 | 3/2010 | Schwartz | |
| 7,697,972 B2 | 4/2010 | Verard et al. | |
| 7,877,128 B2 | 1/2011 | Schwartz | |
| 8,046,052 B2 | 10/2011 | Verard et al. | |
| 8,285,021 B2 | 10/2012 | Boese et al. | |
| 2004/0019447 A1 | 1/2004 | Shachar | |
| 2004/0097806 A1 | 5/2004 | Hunter et al. | |
| 2005/0256398 A1 | 11/2005 | Hastings et al. | |
| 2007/0152974 A1 | 7/2007 | Kim et al. | |
| 2008/0221425 A1 | 9/2008 | Olson et al. | |
| 2010/0198041 A1 | 8/2010 | Christian et al. | |
| 2010/0280363 A1 | 11/2010 | Skarda et al. | |
| 2010/0324414 A1 | 12/2010 | Harlev et al. | |
| 2011/0028848 A1 | 2/2011 | Shaquer et al. | |
| 2013/0190747 A1* | 7/2013 | Koblish | A61B 18/1492 606/41 |
| 2013/0274712 A1 | 10/2013 | Schecter | |
| 2013/0282005 A1 | 10/2013 | Koch et al. | |
| 2013/0288218 A1 | 10/2013 | Mallin et al. | |
| 2013/0336558 A1 | 12/2013 | Manzke et al. | |
| 2014/0275974 A1 | 9/2014 | Samuels | |
| 2014/0276712 A1 | 9/2014 | Mallin et al. | |
| 2015/0302584 A1 | 10/2015 | Brauner et al. | |
| 2016/0045133 A1* | 2/2016 | Balachandran | A61B 5/349 600/509 |
| 2016/0100770 A1 | 4/2016 | Afonso et al. | |
| 2016/0335766 A1 | 11/2016 | Ambwani et al. | |
| 2021/0196312 A1 | 7/2021 | Plewe et al. | |

OTHER PUBLICATIONS

Park et al., Intra-Procedural Imaging of Left Atrium and Pulmonary Veins With Rotational Angiography: A Comparison of Anatomy Obtained by Pre-Procedural Cardiac Computed Tomography and Trans-Thoracic Echocardiography, Apr. 28, 2013 (published online), Apr. 20, 2013 (print date), Int J Cardiovasc Imaging (2013).

* cited by examiner

NAVIGATION GUIDANCE METHOD FOR COMPLEX CATHETERS

CROSS-REFERENCE TO RELATED APPLICATION

This application is a Divisional of U.S. patent application Ser. No. 15/259,683 filed Sep. 8, 2016 VARIABLE GEOMETRY COOLING CHAMBER, the entirety of which is incorporated herein by reference.

STATEMENT REGARDING FEDERALLY SPONSORED RESEARCH OR DEVELOPMENT n/a

TECHNICAL FIELD

The present invention relates to a method and system for determining a target location for a medical device having complex geometry relative to an anatomical feature, and for navigating and positioning the medical device at the target location.

BACKGROUND

In many non-invasive or minimally invasive surgical and treatment procedures, navigating a medical device within a patient's body can be very challenging. Navigation systems are frequently used to help the user identify the location of the medical device and to steer the medical device to the target treatment location. For example, navigation is an important tool in many electrophysiological (EP) procedures because it helps the user understand the placement of the medical device within the cardiac space. Additionally, navigation is often used to place medical devices at areas targeted for thermal treatment and/or ablation.

When the medical device is a focal catheter, for instance, the ablating surface may be directly imaged on the navigation system and there is a close coupling between the navigation and the delivered therapy. However, other medical devices, such as balloon catheters, may have more complex geometry, and navigation electrodes on the device may not exactly correlate with the ablating surface (e.g., the surface of the balloon). Additionally, placement of these complex-geometry devices may be difficult to infer from fluoroscopic imaging or navigation systems relative to the targeted tissue regions.

SUMMARY

The present invention advantageously provides a method and system for determining a target location for a medical device having complex geometry relative to an anatomical feature, and for navigating and positioning the medical device at the target location. A system for determining a target location for a medical device relative to an anatomical feature may include a medical device including and treatment element, such as an expandable treatment element, having a centroid, one or more navigation electrodes, and a longitudinal axis and a navigation system in communication with the one or more navigation electrodes, the navigation system including a processing unit having processing circuitry. The processing circuitry may be configured to define a plane that approximates a surface of the anatomical feature, define a centroid of the anatomical feature, define a vector that is normal to the plane and extends away from the centroid of the anatomical feature, and determine a target location for the treatment element of the medical device based on the vector. The medical device may include a first navigation electrode and a second navigation electrode. Further, the first navigation electrode may be distal to the treatment element and the second navigation electrode may be proximal to the treatment element. The processing circuitry may be further configured to determine a target location for each of the first and second navigation electrodes. The navigation system may further include a display, and the processing circuitry may be further configured to display a first graphical indicator for the target location for the first navigation electrode and display a second graphical indicator for the target location for the second navigation electrode. The first and second graphical indicators may be superimposed on a three-dimensional image of the anatomical feature. The anatomical feature may be a pulmonary vein, and the display may show the first graphical indicator superimposed on the three-dimensional image at a location within the pulmonary vein and may show the second graphical indicator superimposed on the three-dimensional image at a location within a left atrium. The processing circuitry may be further configured to determine the target location for the first navigation electrode according to the equation:

$$e_d = \begin{bmatrix} x_d \\ y_d \\ z_d \end{bmatrix} = \begin{bmatrix} x_b \\ y_b \\ z_b \end{bmatrix} - l_d \begin{bmatrix} a \\ b \\ c \end{bmatrix}$$

where $l_d$ is a distance between the centroid of the treatment element and the first navigation electrode. The processing circuitry may be further configured to determine the target location for the second navigation electrode according to the equation:

$$e_p = \begin{bmatrix} x_p \\ y_p \\ z_p \end{bmatrix} = \begin{bmatrix} x_b \\ y_b \\ z_b \end{bmatrix} + l_p \begin{bmatrix} a \\ b \\ c \end{bmatrix}$$

where $l_p$ is a distance between the centroid of the treatment element and the second navigation electrode. The processing circuitry may be further configured to display a line corresponding to the vector. The processing circuitry may further be configured to determine the target location such that the longitudinal axis of the device lies along the vector.

A system for determining a target location for a medical device relative to a target anatomical feature, such as a pulmonary vein, may include: a medical device including and treatment element having complex geometry and a centroid, a first navigation electrode distal to the treatment element, a second navigation electrode proximal to the treatment element, and a longitudinal axis; a navigation system in communication with the one or more navigation electrodes, the navigation system including a display and a processing circuitry configured to: define a plane that approximates a surface of the target anatomical feature; define a centroid of the target anatomical feature and a boundary of the target anatomical feature; define a vector that is normal to the plane and extends away from the centroid of the target anatomical feature; determine a first target location for the treatment element; determine a second target location for the first navigation electrode and a third target location for the second navigation electrode; and show on the display a first graphical indicator for the target location for the first navigation electrode, a second graphical indicator for the target location for the second navigation electrode, and a line corresponding to the vector, the processing circuitry being configured to determine the first target location in three dimensions according to a first equation:

$$\begin{bmatrix} x_b \\ y_b \\ z_b \end{bmatrix} = \begin{bmatrix} x_0 \\ y_0 \\ z_0 \end{bmatrix} + d \begin{bmatrix} a \\ b \\ c \end{bmatrix}$$

where d is a distance between the centroid of the treatment element and the centroid of the target anatomical feature calculated according to a second equation:

$$d = r_b \cos\left(\sin^{-1}\left(\frac{r_{os,max}}{r_b}\right)\right)$$

where $r_{os,max}$ is a distance between the centroid and the boundary of the anatomical feature and $r_b$ is a distance between the centroid of the treatment element and the boundary of the target anatomical feature, the processing circuitry being configured to determine the second target location in three dimensions according to a third equation:

$$e_d = \begin{bmatrix} x_d \\ y_d \\ z_d \end{bmatrix} = \begin{bmatrix} x_b \\ y_b \\ z_b \end{bmatrix} - l_d \begin{bmatrix} a \\ b \\ c \end{bmatrix}$$

and determining the third target location in three dimensions according to a fourth equation:

$$e_p = \begin{bmatrix} x_p \\ y_p \\ z_p \end{bmatrix} = \begin{bmatrix} x_b \\ y_b \\ z_b \end{bmatrix} + l_p \begin{bmatrix} a \\ b \\ c \end{bmatrix}$$

where $l_d$ is a distance between the centroid of the treatment element and the first navigation electrode and $l_p$ is a distance between the centroid of the treatment element and the second navigation electrode.

A method for navigating a medical device to a target location relative to an anatomical feature may include: obtaining an image of the anatomical feature; defining a plane that approximates a surface of the anatomical feature; defining a centroid of the target anatomical feature and a boundary of the target anatomical feature that each lies in the plane; defining a vector that is normal to the plane and extends away from the centroid of the anatomical feature; determining a target location for a treatment element of the medical device such that a longitudinal axis of the medical device lies along the vector; and displaying the target location on a display of a navigation system. The method may further include displaying the medical device on the display of the navigation system and displaying a line on the display of the navigation system, the display corresponding to the vector. The medical device may have at least one navigation electrode and the treatment element has a centroid, and the method may further comprise providing a navigation system having processing circuitry, the navigation system being in communication with the medical device and determining a recommended distance between the centroid of the treatment element and the centroid of the target anatomical feature. The processing circuitry may be configured to determine the recommended distance between the centroid of the treatment element and the centroid of the target anatomical feature according to the equation:

$$d = r_b \cos\left(\sin^{-1}\left(\frac{r_{os,max}}{r_b}\right)\right)$$

where $r_{os,max}$ is a distance between the centroid of the target anatomical feature and the boundary of the anatomical feature, and $r_b$ is a distance between the centroid of the treatment element and the boundary of the target anatomical feature. The medical device may have a first navigation electrode located distal to the treatment element and a second navigation electrode location proximal to the treatment element, and the method may further comprise determining a recommended location for the first navigation electrode determining a recommended location for the second navigation electrode. The processing circuitry may be configured to determine the recommended location for the first navigation electrode according to the equation:

$$e_d = \begin{bmatrix} x_d \\ y_d \\ z_d \end{bmatrix} = \begin{bmatrix} x_b \\ y_b \\ z_b \end{bmatrix} - l_d \begin{bmatrix} a \\ b \\ c \end{bmatrix}$$

where $l_d$ is a distance between the centroid of the treatment element and the first navigation electrode. The method may further include displaying on the display of the navigation system a first graphical indicator at a location corresponding to the recommended location for the first navigation electrode, the first graphical indicator being superimposed on a three-dimensional image of the target anatomical feature. The processing circuitry may be configured to determine the recommended location for the second navigation electrode according to the equation:

$$e_p = \begin{bmatrix} x_p \\ y_p \\ z_p \end{bmatrix} = \begin{bmatrix} x_b \\ y_b \\ z_b \end{bmatrix} + l_p \begin{bmatrix} a \\ b \\ c \end{bmatrix}$$

where $l_p$ is a distance between the centroid of the treatment element and the second navigation electrode. The method may further include displaying on the display of the navigation system a second graphical indicator at a location corresponding to the recommended location for the second navigation electrode, the second graphical indicator being superimposed on a three-dimensional image of the target anatomical feature.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
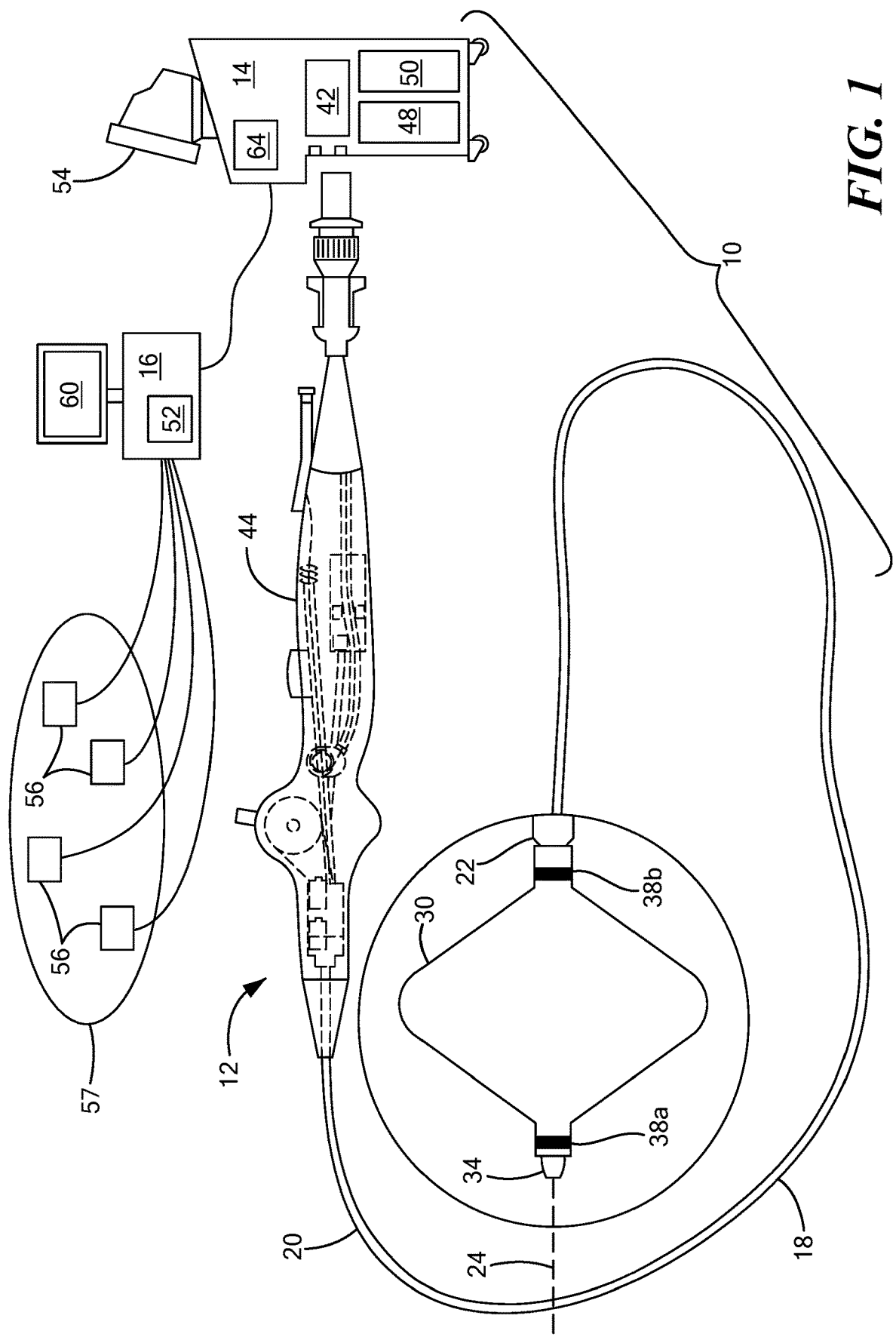
FIG. 1 shows an exemplary medical system that includes a first medical device having complex geometry.
Figure 2:
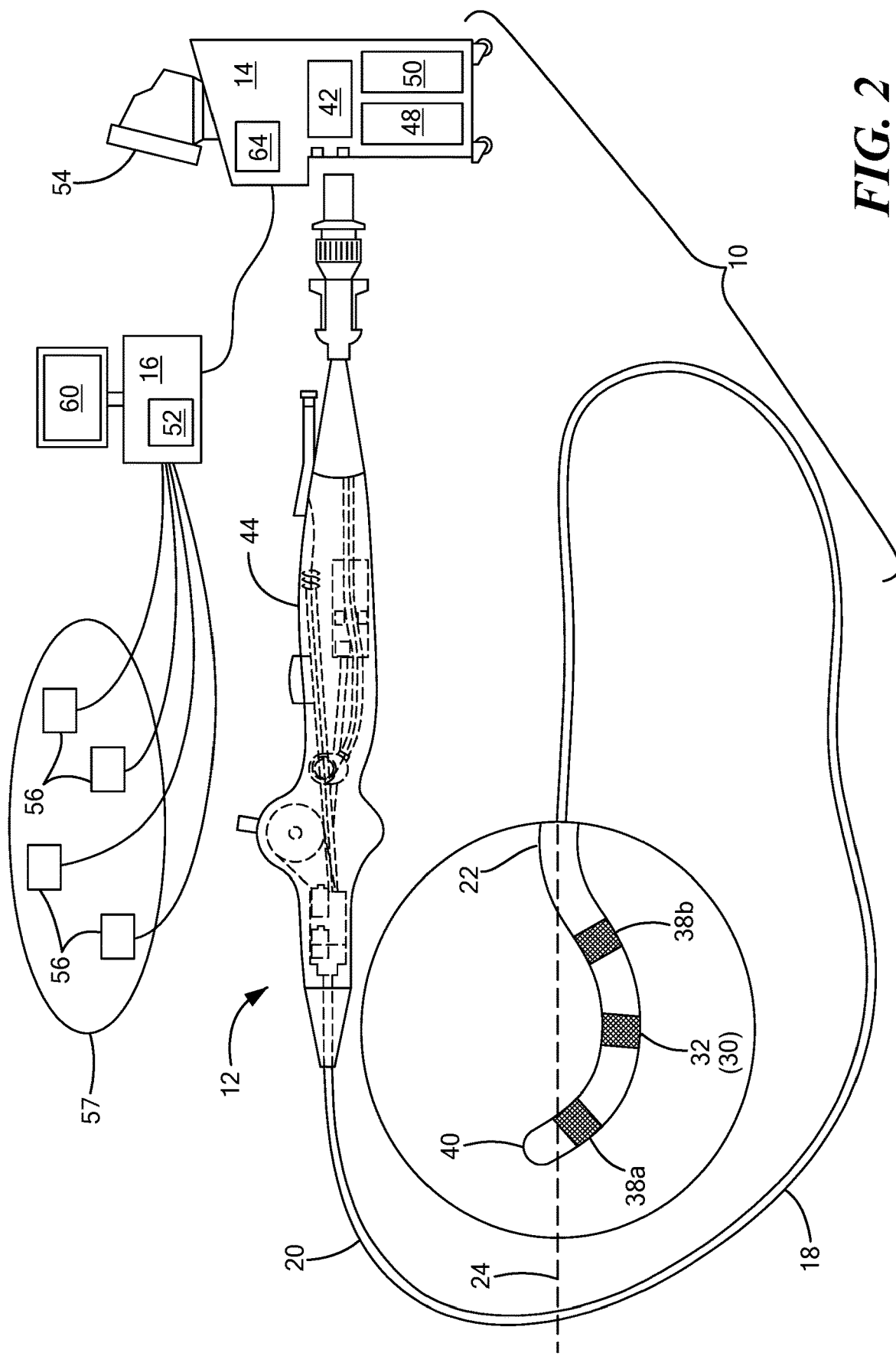
FIG. 2 shows an exemplary medical system that includes a second medical device having complex geometry.

Referring now to the drawing figures in which like reference designations refer to like elements, an embodiment of a medical system constructed in accordance with the principles of the present invention is shown in FIGS. 1 and 2, generally designated as "10." The system 10 generally includes a medical device 12 that may be coupled to a control unit 14 or operating console and a navigation system 16 in communication with the device 12 and the control unit 14. The medical device 12 may generally include one or more diagnostic or treatment elements for energetic, therapeutic, and/or investigatory interaction between the medical device 12 and a treatment site or region. The diagnostic or treatment region(s) may deliver, for example, cryogenic therapy, radiofrequency energy, ultrasound energy, laser energy, or other energetic transfer with a tissue area in proximity to the treatment region(s), including cardiac tissue.

The medical device 12 may be a treatment and/or mapping device. The medical device 12 may include an elongate body 18 passable through a patient's vasculature and/or proximate to a tissue region for diagnosis or treatment. For example, the device 12 may be a catheter that is deliverable to the tissue region via a sheath or intravascular introducer (not shown). The elongate body 18 may define a proximal portion 20, a distal portion 22, and a longitudinal axis 24, and may further include one or more lumens disposed within the elongate body 18 thereby providing mechanical, electrical, and/or fluid communication between the elongate body proximal portion 20 and the elongate body distal portion 28.

The medical device 12 may further include one or more treatment elements 30 at, coupled to, or on the elongate body distal portion 22 that have or are capable of achieving complex geometry during use in the patient. In the non-limiting embodiment shown in FIG. 1, the device may include a treatment element 30 that is expandable, such as one or more balloons. Alternatively, in the non-limiting embodiment shown in FIG. 2, the device may include one or more treatment elements 30 that are not expandable. For example, the device 12 may be a focal catheter that includes one or more electrodes 32 on the distal portion 22, and each electrode may be considered to be a treatment element 30. A focal catheter is shown in FIG. 2. The focal catheter may have a linear configuration, but may also be manipulatable into a curvilinear, looped, spiral, or other configuration, as shown. The expandable treatment element 30 of the system shown in FIG. 1 may be coupled to a portion of the elongate body distal portion 22. The device may optionally include a shaft that is slidably disposed within the elongate body 18 and at least a portion of the shaft may be located within the expandable treatment element 30. The shaft may further include or define a distal tip 34 that may protrude beyond the distal end of the expandable treatment element 30. The expandable treatment element 30 may further include one or more material layers providing for puncture resistance, radiopacity, or the like. If the device 12 is used to delivery cryotherapy (or if used with another energy modality that requires fluid to be delivered to the inner chamber of the treatment element 30), the device may also include one or more fluid injection elements. A device having a non-expandable treatment element may also include one or more fluid injection elements within the elongate body 18 proximate the one or more treatment elements 30 (for example, treatment electrode(s) 32). Further, if the device 12 is used or mapping in addition to or instead of for the delivery of treatment, the device 12 may include one or more mapping electrodes. Although the term "treatment element" is used herein, it will be understood that a mapping element or mapping electrodes could be used instead.

As is discussed in more detail below, the device 12 may also include one or more navigation electrodes 38 that are used by the navigation system 16 to visualize the device 12 on a control unit display and/or a navigation system display. For example, the device 12 shown in FIG. 1 may include a first navigation electrode 38a distal to the expandable portion of the treatment element 30 and a second navigation electrode 38b proximal to the expandable portion of the treatment element 30. Although the navigation electrodes 38a, 38b are shown as being coupled to the portion of the treatment element 30 that is coupled to the elongate body and/or shaft of the device, the navigation electrodes 38a, 38b could alternatively be located distal and proximal to all portions of the treatment element. Likewise, the device 12 shown in FIG. 2 may include a first navigation electrode 38a near the distal tip 40 of the device and a second navigation electrode 38b at a location proximal to the first navigation electrode 38a.

Each treatment electrode 32 and navigation electrode 38 may be electrically conductive segments for conveying an electrical signal, current, or voltage to a designated tissue region and/or for measuring, recording, receiving, receiving, assessing, or otherwise using one or more electrical properties or characteristics of surrounding tissue or other electrodes. The electrodes 32 may be configured in a myriad of different geometric configurations or controllably deployable shapes, and may also vary in number to suit a particular application, targeted tissue structure or physiological feature.

Each treatment electrode 32 may be electrically coupled to an output portion of a power source 42, such as a radiofrequency energy generator or other type of energy generator, and may be in electrical communication with the control unit 14. Each navigation electrode 38 may also be in communication with the navigation system 16 and the control unit 14, and may be configured to receive magnetic or electric signals from the navigation system and transmit signals to the control unit 14 and/or navigation system 16 in a wired and/or wireless connection.

The system 10 may include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The medical device 12 may include a handle 44 coupled to the elongate body proximal portion 20. The handle 44 may include circuitry for identification and/or use in controlling of the medical device 12 or another component of the system. Additionally, the handle 44 may also include connectors 46 that are mateable to the control unit 14 to establish communication between the medical device 12 and one or more components or portions of the control unit 14. The handle 44 may also include one or more actuation or control features that allow a user to control, deflect, steer, or otherwise manipulate a distal portion of the medical device 12 from the proximal portion of the medical device 12. For example, the handle 44 may include one or more components such as a lever or knob 46 for manipulating the elongate body 18 and/or additional components of the medical device 12.

As used herein, the term "control unit 14" for simplicity may include any system components that are not part of the medical device 12 itself, other than components of the navigation system, regardless of whether the component is physically located within or external to the control unit 14. Further, the navigation system 16 may be a standalone system in communication with the control unit 14 or may be contained within or integrated with the control unit 14, even though it is shown as being physically separated from the control unit in FIGS. 1 and 2. The control unit 14 may include one or more components for the delivery of one or more energy modalities for which the system is used. For example, if the system 10 is used to deliver cryotherapy, the control unit 14 may include a supply 48 of a fluid such as a coolant, cryogenic refrigerant, or the like, an exhaust or scavenging system for recovering or venting expended fluid for re-use or disposal, as well as various control mechanisms. In addition to providing an exhaust function for the fluid or coolant supply 48, the control unit 14 may also include pumps, valves, controllers or the like to recover and/or re-circulate fluid delivered to the handle 44, the elongate body 18, and/or the fluid pathways of the medical device 12. Further, a vacuum pump 50 in the control unit 14 may create a low-pressure environment in one or more conduits within the medical device 12 so that fluid is drawn into the conduit(s)/lumen(s) of the elongate body 18, away from the distal portion 22 and towards the proximal portion 20 of the elongate body 18. Additionally or alternatively, the control 14 unit may include a radiofrequency generator or power source 42 as a treatment or diagnostic mechanism in communication with the treatment electrode(s) 32 of the medical device 12. The radiofrequency generator 42 may have a plurality of output channels, with each channel coupled to an individual treatment electrode 32. The radiofrequency generator 42 may be operable in one or more modes of operation.

The control unit 14 may include one or more controllers, processors, and/or software modules 52 containing circuitry configured to execute instructions or algorithms to provide for the automated operation and performance of the features, sequences, calculations, or procedures described herein. For example, the processor(s) 52 may be configured, programmed, or programmable to perform the calculations and make the determinations discussed in greater detail below to identify a target location for a medical device relative to an anatomical feature, even if that device has complex geometry that has traditionally made the process challenging. Further, the control unit 14 may include one or more user input devices, controllers, and displays 54 for collecting and conveying information from and to the user.

The navigation system 16 may be any commercially available navigation system suitable for use with the control unit 14, device 12, and type of procedure. As a non-limiting example, the navigation system 16 may include a plurality of surface electrodes 56, a reference electrode (not shown), and a processing unit 58 that collects and processes signals from the navigation electrodes 38, and a display that displays to the user the location of the device 12 within the patient's body 57 and/or relative to the target anatomical feature (for example, a pulmonary vein ostium), and recommended landing zones for the device 12. The processing unit 58 may include processing circuitry including a memory and a processor, the memory in communication with the processor and having instructions that, when executed by the processor, configure the processor to perform the calculations and determinations discussed herein. Additionally or alternatively, this information may be displayed on the display 64 of the control unit 14. The navigation system 16 may also include an energy generator (not shown) for delivering energy to the plurality of surface electrodes 56. Alternatively, the navigation system may be in communication with the control unit power source 42. It will be understood that the calculations discussed herein may additionally or alternatively be performed by one or more processors 64 within the control unit 14.

As shown in FIGS. 1 and 2, the surface electrodes 56 may be applied to the patient's skin and may deliver relatively low-frequency radiofrequency energy through the patient toward the procedure site, current device location, or the target anatomical feature. The navigation electrode(s) 38 on the device 12 may each record a voltage and impedance from this energy and transmit data to the processing unit 58, which may then determine a position of the electrode(s) 38, and therefore the device 12, within the patient. The processing unit 58 may perform this calculation many times during a procedure, frequently updating the registered location and displaying such to the user so the user can visualize the location of the device relative to the target anatomical feature in real time. However, it will be understood that the navigation electrode(s) 38 may be configured to be used with navigation systems other than impedance-based systems, such as navigation systems that are magnetic field based, hybrid impedance/magnetic field based, ultrasound field based, and/or radiation based, and/or navigation systems that may be developed in the future.

Figure 3:
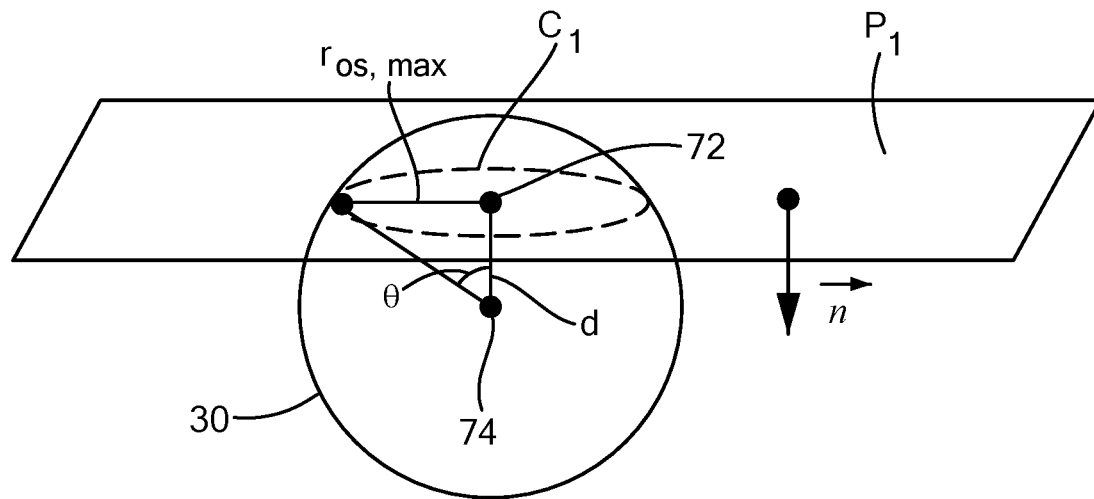
FIG. 3 shows a geometric representation of a calculation of optimal placement of a treatment element of a medical device.

Now referring to FIG. 3, a geometric representation of the calculation performed by the system 10 is shown. It will be understood that the elements of FIG. 3 are not drawn to scale and are meant only to show the geometric relationship between components used to calculate an optimal device position relative to a target anatomical feature 70. The system 10 may identify one or more target anatomical features, such as pulmonary vein(s), prior to or during the procedure. A target pulmonary vein ostium, for example, may be manually defined by the user or automatically or semi-automatically defined by the control unit 14 or navigation system 16 using an algorithm executed by the processor(s) 64 or processing unit 58. When executed, the algorithm may be used to trace the centroid 72 of each pulmonary vein as the pulmonary vein enters the left atrium, and it may then be used identify the various planes and contours of each pulmonary vein. Subsequently, the algorithm may be used to derive the axis and location of at least one target position (which may be referred to herein as a "landing zone") based on design information for the device 12 being used. This information may include measurements such as $r_b$, $l_d$, and $l_p$, defined and discussed below.

The process performed by the processing unit 58 of the navigation system 16 is now discussed in more detail. However, if the algorithm for the initial identification of the target anatomical feature is executed by the processor(s) 64 of the control unit 14, this information will be transmitted from the control unit 14 to the navigation system 16, which may then perform the calculations/execute further algorithm(s) for determining the optimal device position for the procedure.

First, the processing unit 58 of the navigation system 16 may define or determine a plane $P_1$ that approximates a surface of the target anatomical feature 70. For example, the plane may approximate the pulmonary vein ostium, which may not naturally be perfectly planar. The plane may be expressed by the following equation:

$$ax + by + cz + d = 0 \quad (1)$$

The plane described by equation (1) is described by a normalized vector perpendicular to the surface of the plane expressed as $[a\ b\ c]^T$.

The processing unit 58 may then determine a border $C_1$ of the target anatomical feature 70, such as a pulmonary vein ostium, and calculate the location of the centroid 72 of the border $C_1$. As the border $C_1$ may not be perfectly circular or symmetric, the centroid may be calculated as the arithmetic mean (average) of all the points in the shape. The centroid of a pulmonary vein ostium $(x_0, y_0, z_0)$ may be calculated as the point lying in the centroid of the surface on plane $P_1$ bounded by $C_1$ (as shown in FIG. 3).

The processing unit 58 may then define or determine a vector $\vec{n}$ that is normal to the plane $P_1$ and extends away from the target anatomical feature 70. For example, although FIG. 3 shows the vector $\vec{n}$ as extending from a point in the plane that is not the centroid of the target anatomical feature, the vector $\vec{n}$ may have a starting point within plane $P_1$ that is the centroid 72 location, and may extend away from the pulmonary vein ostium and into the left atrium. The vector $\vec{n}$ may be expressed by the following equation:

$$\vec{n} = \begin{bmatrix} x_0 \\ y_0 \\ z_0 \end{bmatrix} + \delta \begin{bmatrix} a \\ b \\ c \end{bmatrix} \quad (2)$$

where parameters a, b, and c are defined by the plane $P_1$, $\delta$ is a scaling factor to create a line in the direction of the vector. $[x_0, y_0, z_0]^T$ of equation (2) represents the centroid 72 shown in FIG. 3.

Further, the treatment element 30 shown in FIG. 3 is an expandable treatment element, such as a balloon. Even though the treatment element 30 is shown as being circular (or spherical), it will be understood that this is for simplicity and that that treatment element may have other shapes, sizes, and configurations. The treatment element 30 may have a center 74 if it is a circular treatment element (or centroid of a non-circular treatment element) $(x_b, y_b, z_b)$ and a radius $r_b$ between the center/centroid 74 of the treatment element and the border $C_1$ of the pulmonary vein ostium. As shown in FIG. 3, the distance d between the centroid 72 of, for example, the pulmonary vein ostium $(x_0, y_0, z_0)$ and the center/centroid 74 of the treatment element $(x_b, y_b, z_b)$ the and the distance $r_{os,max}$ between the centroid 72 of the pulmonary vein ostium and the outermost reach of the border $C_1$ of the pulmonary vein ostium may be calculated. The optimal distance d between the center/centroid 74 of the treatment element 30 and the centroid 72 of the pulmonary vein ostium may be calculated using the following equation:

$$d = r_b \cos\left(\sin^{-1}\left(\frac{r_{os,max}}{r_b}\right)\right) \quad (3)$$

Although $r_{os,max}$ is shown as the distance between the center/centroid 72 of the pulmonary vein ostium and the border $C_1$, in FIG. 3, $r_{os,max}$ may alternatively be calculated as a distance between a point along the longitudinal axis 24 of the device (that passes through the center/centroid 72 of the pulmonary vein ostium and the navigation electrode(s) 38), and the border $C_1$.

The processing unit 58 may use these calculations to recommend at least one target position or "landing zone" for the device 12. For example, the processing unit 58 may recommend that the device may be positioned such that its longitudinal axis 24 lies along the vector $\vec{n}$ that extends away from the centroid 72 of the target anatomical feature, such as a pulmonary vein ostium, and into the left atrium. In other words, the center/centroid 74 of the treatment element 30 $(x_b, y_b, z_b)$ may be calculated to be normal to the surface of the plane $P_1$, passing through the centroid 72 of the pulmonary vein ostium $(x_0, y_0, z_0)$. Thus, the location of the center/centroid 74 of the treatment element 30 $(x_b, y_b, z_b)$ may be calculated using the following equation (where d is calculated as in equation (3)):

$$\begin{bmatrix} x_b \\ y_b \\ z_b \end{bmatrix} = \begin{bmatrix} x_0 \\ y_0 \\ z_0 \end{bmatrix} + d \begin{bmatrix} a \\ b \\ c \end{bmatrix} \quad (4)$$

The one or more navigation electrodes 38 may be used to visualize the location of the device 12 using the navigation system 16 and/or a mapping system (not shown). Further, using the exact location(s) of the navigation electrode(s) 38 on the device 12, the processing unit 58 may calculate an optimal location for the each electrode 38. For example, the optimal location of a navigation electrode 38 may be calculated relative to the center/centroid 74 of the treatment element 30 $(x_b, y_b, z_b)$ along the direction of the vector $\vec{n}$. Additionally, if the device 12 includes a distal first navigation electrode 38a ($e_d$) and a proximal second navigation electrode 38b ($e_p$), an optimal location for each of these electrodes may also be calculated. If the distance between the center/centroid 74 of the treatment element 30 and the distal navigation electrode 38a ($e_d$) is $l_d$ and the distance between the center/centroid 74 of the treatment element 30 and the proximal navigation electrode 38b ($e_p$) is $l_p$, the optimal location of $e_d$ and $e_p$ may be calculated using the following equations:

$$e_d = \begin{bmatrix} x_d \\ y_d \\ z_d \end{bmatrix} = \begin{bmatrix} x_b \\ y_b \\ z_b \end{bmatrix} - l_d \begin{bmatrix} a \\ b \\ c \end{bmatrix} \quad (5)$$

$$e_p = \begin{bmatrix} x_p \\ y_p \\ z_p \end{bmatrix} = \begin{bmatrix} x_b \\ y_b \\ z_b \end{bmatrix} + l_p \begin{bmatrix} a \\ b \\ c \end{bmatrix} \quad (6)$$

In equation (5), the placement of $e_d$ would be distal (as the term is used for the device 12) to the center/centroid 74 of the treatment element 30, in the direction of the target anatomical feature 70, while $e_p$ would be proximal of both the centroid 72 of the anatomical feature 70 and the center/centroid 74 of the treatment element 30. Parameters $r_b$, $l_d$, and $l_p$ may be known for the particular device being used.

The navigation system display 60 and/or the control unit display 54 may show device placement graphical indicators 78 for both the optimal location of each of the one or more navigation electrodes 58 and may show the real-time coordinates of the navigation electrode(s) 58. Thus, the user could see the recommended "landing zones" for each of the electrode(s) and could then navigate the device to achieve the recommended device location before beginning the treatment and/or mapping procedure at the target site. Positioning the device at the recommended location may help ensure proper placement of the treatment element 30 with respect to depth as well as orientation, which may create an optimal treatment profile in the target anatomical feature 70.

The navigation system display 60 and/or the control unit display 54 may show an image of an area proximate the target anatomical feature 70, such as the cardiac space surrounding one or more pulmonary veins, and the graphical indicators may be superimposed on this image. The image may be obtained from an imaging system such as a computed tomography (CT) system, a magnetic resonance imaging (MRI) system, or other system suitable for creating images of locations within a patient's body. For example, the imaging system may create images in Digital Imaging and Communications in Medicine (DICOM) format. The imaging system may be in communication with and digitally transmit images to the navigation system 16 and/or the control unit 14 for further processing. Alternatively, images recorded by the imaging system may be recorded and transferred to the navigation system 16 and/or the control unit 14 by a user. The device 12 may also be shown, as well as the navigation electrodes 38. Optionally, the graphical indicators or "landing zones" 78 for each of the navigation electrodes 38 may be differentiated in some way for enhanced visualization. For example, the graphical indicator 78 for each electrode may have a different color, fill pattern, numerical reference number, or the like.

Figure 4:
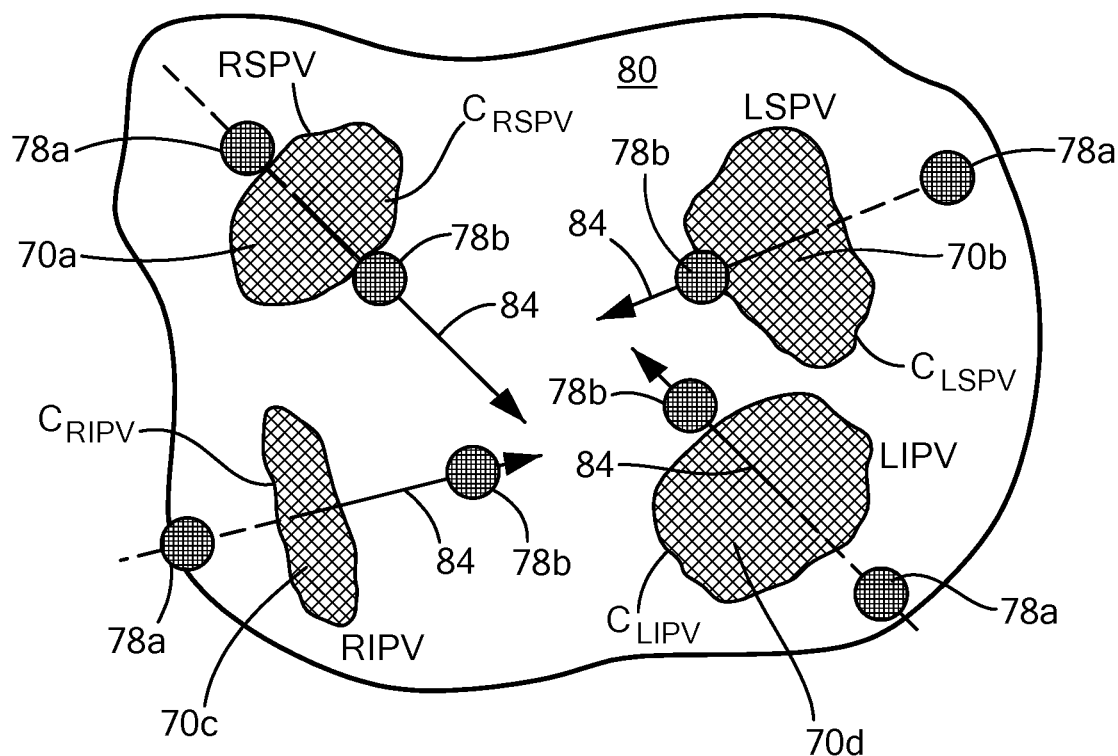
FIG. 4 shows an exemplary simplified representation of recommended device placement indicators.

Referring now to FIG. 4, an exemplary simplified representation of recommended treatment device placement locations is shown. The target anatomical feature 70 in FIG. 4 may be any or all of four pulmonary veins located on the left atrial wall 80 having border C: the right superior pulmonary vein (RSPV) 70*a* with border $C_{RSPV}$; the left superior pulmonary vein (LSPV) 70*b* with border $C_{LSPV}$; the right inferior pulmonary vein (RIPV) 70*c* with border $C_{RIPV}$; and/or the left inferior pulmonary vein (LIPV) 70*d* with border $C_{LIPV}$. The device 12 may have a distal first navigation electrode 38*a* ($e_d$) and a proximal second navigation electrode 38*b* ($e_p$). The display may show a vector line 84, a graphical indicator 78*a* for the distal navigation electrode 38*a*, and a graphical indicator 78*b* for the proximal navigation electrode 38*b* for each pulmonary vein. Although a simplified view is shown in FIG. 4, it will be understood that the actual displayed image may be three dimensional and may show additional tissue characteristics, anatomical features, or the like. Further, as the image is rotated in space, the pulmonary vein ostia, vector lines, and graphical indicators rotate accordingly.

Figure 5:
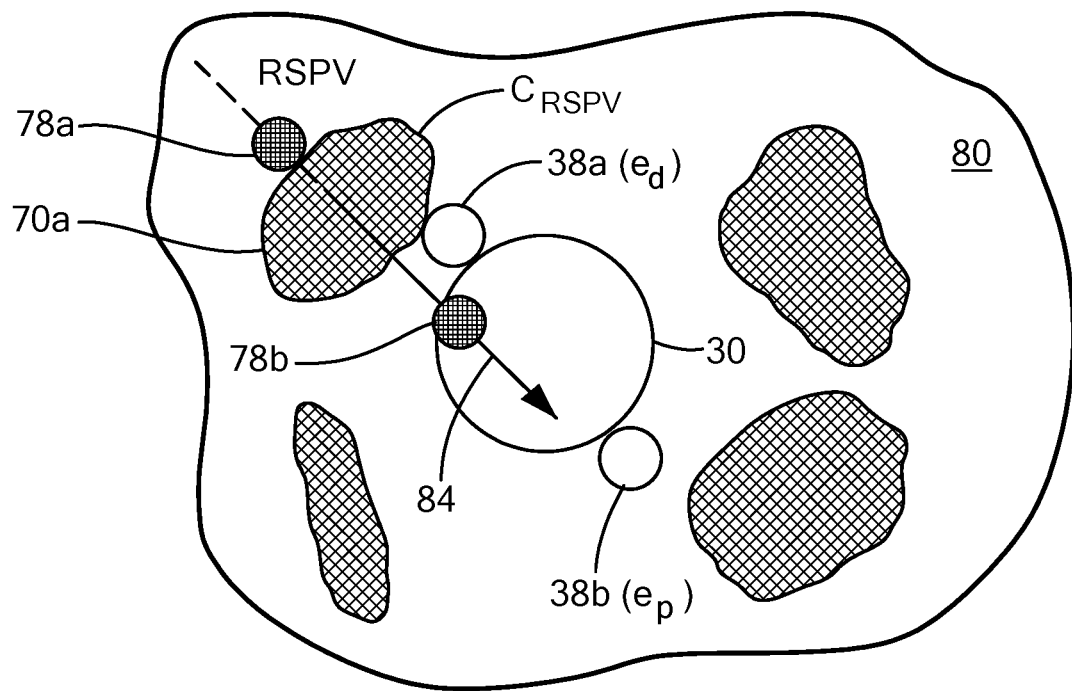
FIGS. 5-7 together show an exemplary simplified representation of placement of a treatment element of a medical device at recommended landing zones.
Figure 6:
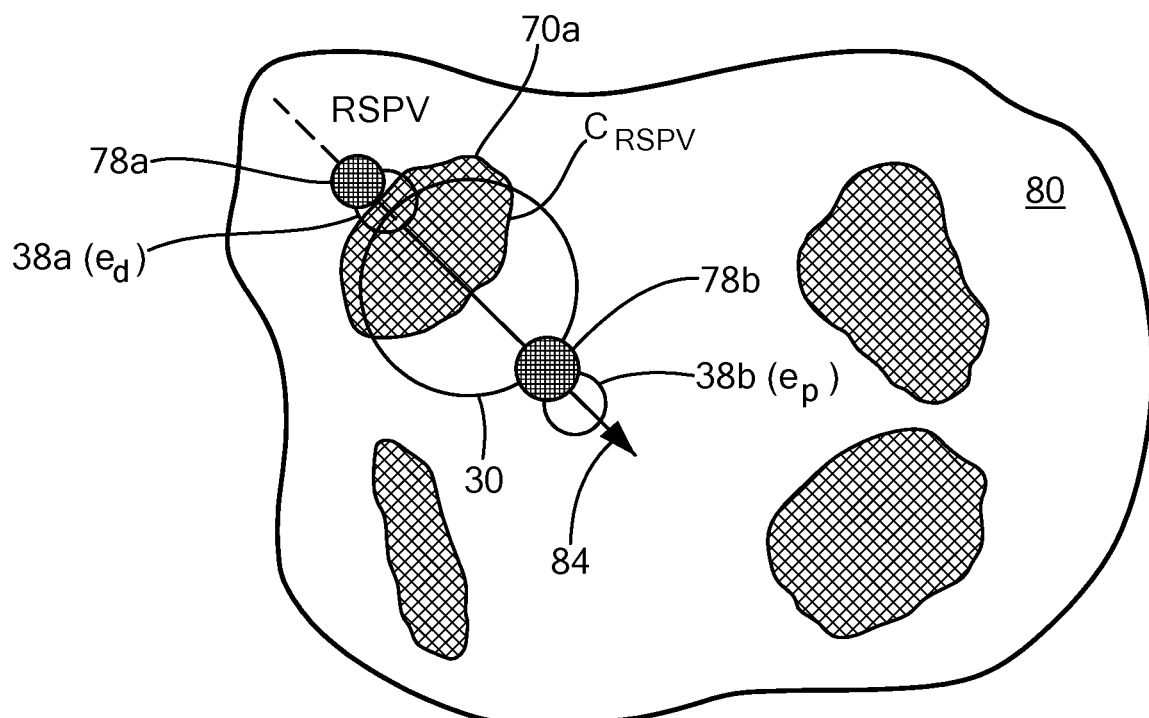
Figure 7:
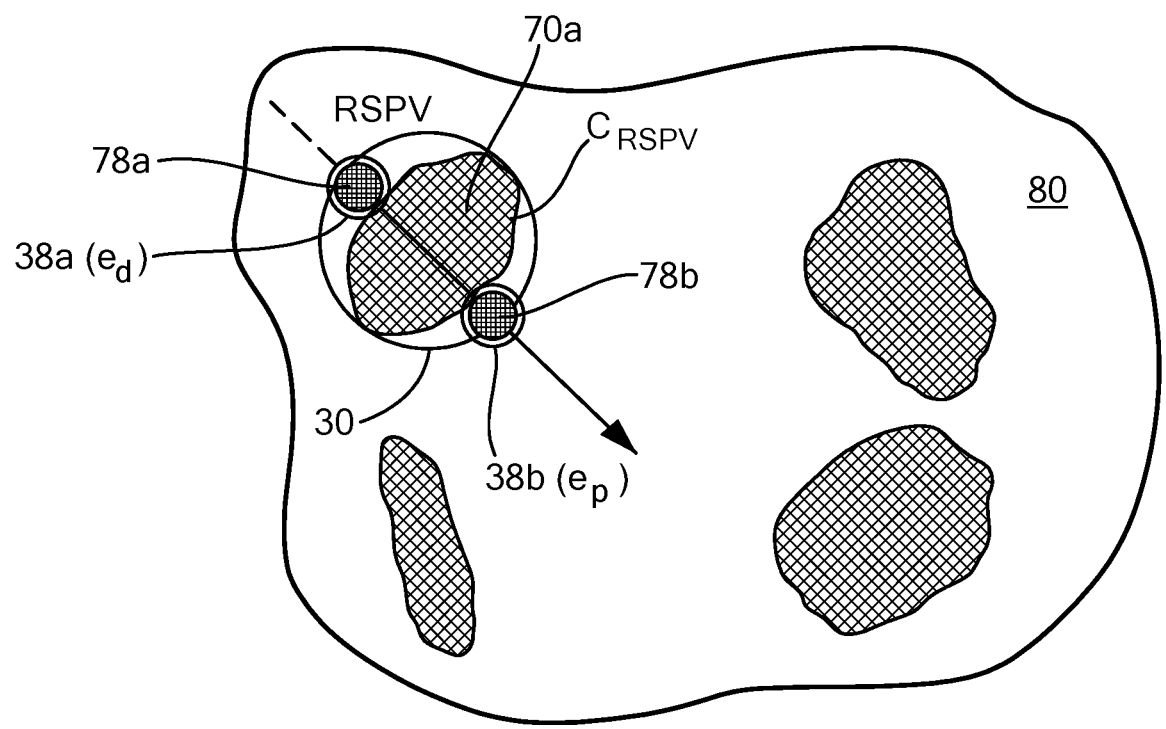

Now referring to FIGS. 5-7, an exemplary placement of a treatment element of a device at recommended target positions or "landing zones" is shown. The images shown in FIGS. 5-7, like that shown in FIG. 4, are simplified representations of what may be shown on a system display in more detail. The display 54 and/or 60 may show an area of tissue surrounding the target anatomical feature(s) 70, such as a left atrial wall 80, the target anatomical feature(s) 70, the device treatment element 30, a vector line 84, and at least one graphical indicator 78 for the recommended landing zone(s). In the images shown in FIGS. 5-7, the device 12 may include two navigation electrodes 38*a*, 38*b* proximal and distal to the treatment element 30, labeled as $e_d$ and $e_p$ in the figures. Consequently, the display may show two graphical indicators 78*a*, 78*b*, corresponding to the two navigation electrodes 38*a*, 38*b*, respectively.

In FIG. 5, the display may allow the user to visualize the device 12 within the treatment space, for example, the left atrium. The user may then use this image to align the longitudinal axis 24 of the device with the vector line 84. In other words, the user may use the image to approach the target anatomical feature, here a right superior pulmonary vein ostium 70*a*, at the recommended location. In FIG. 6, the display may allow the user to visualize the device 12 moving closer to the pulmonary vein ostium 70*a* and recommended alignment. The objective may be to align the navigation electrodes 38*a*, 38*b* ($e_d$ and $e_p$) with the graphical indicators 78*a*, 78*b*, respectively. Finally, in FIG. 7, the display may allow the user to visualize the device 12 positioned at the optimal treatment location, wherein the navigation electrodes 38*a*, 38*b* are properly aligned with the graphical indicators 78*a*, 78*b*, respectively. As a non-limiting example, the first graphical indicator 78*a* may be a small distance inside the pulmonary vein whereas the second graphical indicator 78*b* may be a distance away from the pulmonary vein, within the left atrium. This may ensure that a portion of the treatment element 30 having the widest diameter is positioned at the pulmonary vein ostium, occluding the pulmonary vein. If the device is used to deliver cryotreatment, this alignment may help ensure that a circular ablation lesion is created at the pulmonary vein ostium. Further, the user may monitor alignment of the device during the procedure in real time.

Once the treatment element 30 of the device 12 is properly aligned, the treatment procedure may begin. If the device is a cryotreatment device, a known or estimated cooling profile of the treatment element 30 and placement of the treatment element 30 relative to the target anatomical feature may be used to provide additional feedback on the cooling profile across the contacted tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for navigating a medical device to a target location relative to an anatomical structure within which the medical device is inserted, the medical device having a treatment element with a known positioned between two navigation electrodes, the method comprising:
obtaining an image of the anatomical structure;
defining a plane that approximates a surface of the anatomical structure;
defining a centroid of the target anatomical structure and a boundary of the target anatomical structure that each lies in the plane;
defining a vector that is normal to the plane and extends away from the centroid of the anatomical structure;
determining a target location for the treatment element of the medical device, the target location for the treatment element having a longitudinal axis of the medical device lying along the vector;
displaying a graphical indicator of the target location on a display of a navigation system; and
navigating the medical device relative to the anatomical structure such that the treatment element is aligned with the graphical indicator of the target location displayed on the display of the navigation system.

2. The method of claim 1, the method further comprising:
displaying a second graphical indicator of current location of the medical device on the display of the navigation system; and
displaying a line on the display of the navigation system, the line corresponding to the vector.

3. The method of claim 2, wherein the treatment element has a centroid, the method further comprising:
providing the navigation system having a processing circuitry, the navigation system being in communication with the medical device; and
determining a recommended distance between the centroid of the treatment element and the centroid of the target anatomical structure.

4. The method of claim 3, wherein the processing circuitry is configured to determine the recommended distance between the centroid of the treatment element and the centroid of the target anatomical structure according to the equation:

$$d = r_b \cos\left(\sin^{-1}\left(\frac{r_{os,max}}{r_b}\right)\right)$$

where $r_{os,max}$ is a distance between the centroid of the target anatomical structure and the boundary of the anatomical structure and $r_b$ is a distance between the centroid of the treatment element and the boundary of the anatomical structure.

5. The method of claim 3, wherein the two navigation electrodes include a first navigation electrode and a second navigation electrode, wherein the processing circuitry is configured to determine a recommended location for the first navigation electrode according to the equation:

$$e_d = \begin{bmatrix} x_d \\ y_d \\ z_d \end{bmatrix} = \begin{bmatrix} x_b \\ y_b \\ z_b \end{bmatrix} - l_d \begin{bmatrix} a \\ b \\ c \end{bmatrix}$$

where $l_d$ is a distance between the centroid of the treatment element and the first navigation electrode.

6. The method of claim 5, wherein the processing circuitry is configured to determine a recommended location for the second navigation electrode according to the equation:

$$e_p = \begin{bmatrix} x_p \\ y_p \\ z_p \end{bmatrix} = \begin{bmatrix} x_b \\ y_b \\ z_b \end{bmatrix} + l_p \begin{bmatrix} a \\ b \\ c \end{bmatrix}$$

where $l_p$ is a distance between the centroid of the treatment element and the second navigation electrode.

7. The method of claim 3, wherein the two navigation electrodes include a first navigation electrode located distal to the treatment element and a second navigation electrode location proximal to the treatment element, the method further comprising:
determining a recommended location for the first navigation electrode; and
determining a recommended location for the second navigation electrode.

8. The method of claim 7, further comprising displaying on the display of the navigation system a third graphical indicator at a location corresponding to the recommended location for the second navigation electrode, the third graphical indicator being superimposed on a three-dimensional image of the target anatomical structure.

9. The method of claim 8, further comprising displaying on the display of the navigation system a fourth graphical indicator at a location corresponding to the recommended location for the first navigation electrode, the fourth graphical indicator being superimposed on the three-dimensional image of the target anatomical structure.

10. The method of claim 9, wherein the anatomical structure is a pulmonary vein, and wherein displaying on the display the fourth graphical indicator superimposed on the three-dimensional image includes displaying the fourth graphical indicator at a location within the pulmonary vein and wherein displaying on the display the third graphical indicator superimposed on the three-dimensional image includes displaying the third graphical indicator at a location within a left atrium.

11. A method for navigating a medical device to a target location relative to an anatomical structure within which the medical device is inserted, the method comprising:
obtaining an image of the anatomical structure;
defining a plane that approximates a surface of the anatomical structure;
defining a centroid of the target anatomical structure and a boundary of the target anatomical structure that each lies in the plane;
determining a vector that is normal to the plane and extends away from the centroid of the anatomical structure;
determining a first target location for a treatment element of the medical device, the first target location for the treatment element having a longitudinal axis of the medical device lying along the vector;
determining a second target location for a first navigation electrode of the medical device and a third target location for a second navigation electrode of the medical device, the treatment element having a centroid and disposed between the first navigation electrode and the second navigation electrode with a known first distance between the centroid of the treatment element and the first navigation electrode and a known second distance between the centroid of the treatment element and the second navigation electrode;
displaying a first graphical indicator for the first target location on a display of a navigation system, displaying a second graphical indicator for the second target location on the display of the navigation system, and displaying a third graphical indicator for the third target location on the display of the navigation system; and navigating the medical device relative to the anatomical structure such that the treatment element is aligned with at least one of a group consisting of the first target location, the second target location, and the third target location displayed on the display of the navigation system.

12. The method of claim 11, wherein displaying on the display the first graphical indicator and the second graphical indicator includes displaying the first graphical indicator and the second graphical indicator superimposed on a three-dimensional image of the anatomical structure.

13. The method of claim 12, wherein the anatomical structure is a pulmonary vein, and wherein displaying the first graphical indicator and the second graphical indicator superimposed on the three-dimensional image of the anatomical structure includes showing the first graphical indicator superimposed on the three-dimensional image at a location within the pulmonary vein and showing the second graphical indicator superimposed on the three-dimensional image at a location within a left atrium.

14. The method of claim 11, the method further comprising:
displaying a fourth graphical indicator of a current location of the medical device on the display of the navigation system; and
displaying a line on the display of the navigation system, the line corresponding to the vector.

15. The method of claim 14, wherein the treatment element has a centroid, the method further comprising:
providing the navigation system having a processing circuitry, the navigation system being in communication with the medical device; and
determining a recommended distance between the centroid of the treatment element and the centroid of the target anatomical structure.

16. The method of claim 15, wherein the processing circuitry is configured to determine the recommended distance between the centroid of the treatment element and the centroid of the target anatomical structure according to the equation:

$$d = r_b \cos\left(\sin^{-1}\left(\frac{r_{os,max}}{r_b}\right)\right)$$

where $r_{os,max}$ is a distance between the centroid of the target anatomical structure and the boundary of the anatomical structure and $r_b$ is a distance between the centroid of the treatment element and the boundary of the anatomical structure.

17. The method of claim 14, wherein the processing circuitry is configured to determine the first target location for the first navigation electrode according to the equation:

$$e_d = \begin{bmatrix} x_d \\ y_d \\ z_d \end{bmatrix} = \begin{bmatrix} x_b \\ y_b \\ z_b \end{bmatrix} - l_d \begin{bmatrix} a \\ b \\ c \end{bmatrix}$$

where $l_d$ is a distance between the centroid of the treatment element and the first navigation electrode.

18. The method of claim 14, wherein the processing circuitry is configured to determine the second target location for the second navigation electrode according to the equation:

$$e_p = \begin{bmatrix} x_p \\ y_p \\ z_p \end{bmatrix} = \begin{bmatrix} x_b \\ y_b \\ z_b \end{bmatrix} + l_p \begin{bmatrix} a \\ b \\ c \end{bmatrix}$$

where $l_p$ is a distance between the centroid of the treatment element and the second navigation electrode.

19. A method for navigating a medical device to a target location relative to an anatomical structure within which the medical device is inserted, the method comprising:
obtaining an image of the anatomical structure;
defining a plane that approximates a surface of the anatomical structure;
defining a centroid of the target anatomical structure and a boundary of the target anatomical structure that each lies in the plane;
defining a vector that is normal to the plane and extends away from the centroid of the anatomical structure;
determining a first target location for a treatment element of the medical device, the first target location for the treatment element having a longitudinal axis of the medical device lying along the vector, the treatment element having a centroid, first navigation electrode, and a second navigation electrode, the treatment element disposed between the first navigation electrode and the second navigation electrode with a known first distance between the centroid of the treatment element and the first navigation electrode and a known second distance between the centroid of the treatment element and the second navigation electrode;
providing the navigation system having a processing circuitry, the navigation system being in communication with the medical device;
determining a recommended distance between the centroid of the treatment element and the centroid of the target anatomical structure;
determining a second target location for the first navigation electrode of the medical device and a third target location for the second navigation electrode of the medical device, the first navigation electrode being located distal to the treatment element and the second navigation electrode in a location proximal to the treatment element;
displaying a first graphical indicator for the first target location on a display of a navigation system,
displaying a second graphical indicator for the second target location on the display of the navigation system;
displaying a third graphical indicator for the third target location on the display of the navigation system, the first graphical indicator and the second graphical indicator superimposed on a three-dimensional image of the anatomical structure;
displaying a fourth graphical indicator of a current location of the medical device on the display of the navigation system;
displaying a line on the display of the navigation system, the line corresponding to the vector; and
repeatedly updating information provided via the display as the current location of the medical treatment device changes.

* * * * *